United States Patent [19]

Haber et al.

[11] Patent Number: 4,802,479
[45] Date of Patent: * Feb. 7, 1989

[54] HAND-HELD INSTRUMENT FOR IMPLANTING, DISPENSING, AND INFLATING AN INFLATABLE MEMBRANE

[75] Inventors: Terry M. Haber, Lake Forest; William H. Smedley, Lake Elsinore, both of Calif.

[73] Assignee: C. R. Bard, Inc., Murray Hill, N.J.

[*] Notice: The portion of the term of this patent subsequent to Aug. 18, 2004 has been disclaimed.

[21] Appl. No.: 925,163

[22] Filed: Oct. 31, 1986

[51] Int. Cl.[4] .............................................. A61B 19/00
[52] U.S. Cl. ........................... 128/344; 128/DIG. 25; 604/97
[58] Field of Search ................... 128/1 R, 305, 305.3, 128/311, 325, 328, 341, 343, 344, 348.1, 330, DIG. 25, 329, 345; 604/61, 97–99, 158, 223, 272–274, 162, 104–109, 51

[56] References Cited

U.S. PATENT DOCUMENTS

| | | | |
|---|---|---|---|
| 2,042,900 | 6/1936 | James | 604/106 |
| 2,854,982 | 10/1958 | Pagano | 604/101 |
| 2,856,920 | 10/1958 | Indelicato | 128/129 |
| 3,795,246 | 3/1974 | Sturgeon | 604/99 |
| 3,895,636 | 7/1975 | Schmidt | 128/305 |
| 3,989,049 | 11/1976 | Yoon | 128/325 |
| 4,429,724 | 2/1984 | Dorros et al. | 128/344 |
| 4,517,979 | 5/1985 | Pecenka | 128/344 |
| 4,557,255 | 12/1985 | Goodman | 128/344 |
| 4,686,962 | 8/1987 | Haber | 128/325 |

*Primary Examiner*—Dalton L. Truluck
*Attorney, Agent, or Firm*—Morland C. Fischer

[57] ABSTRACT

A compact, hand-held instrument by which to permit a physician to accurately and controllably implant, dispense, and inflate an inflatable membrane at a predetermined target area within the tissues of a patient. In a preferred embodiment of the invention, the inflatable membrane is a genitourinary prosthesis, and the targeted area lies within the corpus spongiousum surrounding the urethra to enable a patient to overcome urinary incontinence by means of increasing both localized tissue volume and passive occlusive pressure upon the urethral mucosa. The instrument includes a trocar assembly having a plurality of telescoping trocar members which may be either retracted for dilating a tunnel through the urethral tissues of the patient or expanded for placing, dispensing and inflating the membrane at the end of the tunnel. The membrane is percutaneously infused with and inflated by material (e.g. biocompatible fluid) supplied from a vernier hypodermic syringe to a hollow, non-coring needle, which needle carries the membrane and communicates with the syringe.

20 Claims, 5 Drawing Sheets fig4 fig5 fig6 fig7 fig8 fig9 fig10 fig 11 fig 12 fig 13 fig 14

HAND-HELD INSTRUMENT FOR IMPLANTING, DISPENSING, AND INFLATING AN INFLATABLE MEMBRANE

BACKGROUND OF THE INVENTION

1. Field of the Invention

This invention relates to a compact, hand-held instrument which enables a physician to perform a relatively quick and simple procedure to accurately and controllably implant, dispense and inflate an inflatable membrane (e.g. a genitourinary prosthesis) at a predetermined target area within the urethral tissues of a patient to enable a patient to overcome urinary incontinence by means of increasing both localized tissue volume and passive occlusive pressure proximal to the periurethral tissues of the proximal corpus spongiousum.

2. Prior Art

As will be known to those skilled in the art, in cases where the natural sphincter muscles of a patient have been surgically excised, damaged by disease or compromised by physical trauma, an artificial prosthetic sphincter has often been implanted so that occlusive pressure may be applied to the urethra to restore continence. Artificial sphincters are well-known and specific examples thereof will not be listed. However, the implantation of an artificial sphincter commonly requires a surgical procedure which necessitates the hospitalization of the patient. Such a procedure is relatively complex and expensive, and usually requires six to eight weeks or more of recovery time. Accordingly, both the patient and his physician face approximately two months of delay before being able to activate the prothesis to ascertain whether the surgery has been successful and the patient is continent. More particularly, because of the swollen and aggravated condition of edema of the urethral tissues during and for a period subsequent to surgery, the physician cannot precisely match the occlusive pressure available from the prosthetic sphincter to the patient's urethra. Therefore, at the time of implant, the physician must estimate the required minimal occlusive pressure needed to achieve urethral coaptation in that particular patient. As a consequence of such estimate, sphincteric mechanisms are often improperly fitted or selected with inaccurate pressure ranges, so that the occlusive pressures generated by such mechanisms are either insufficient to successfully achieve continence or excessive to the point of causing ischemia and subsequent necrosis and erosion of urethral tissue. Excessive occlusive forces may undesirably minimize arteriovascular blood flow to the urethra and thereby cause ischemia and subsequent erosion of the delicate tissues. What is more, if the implant surgery should prove to be unsuccessful (i.e. the maximum occlusive pressure to be generated by the sphincter is insufficient to hold the patient incontinent or the sphincter malfunctions mechanically), then additional surgery becomes necessary to provide sphincteric adjustment, repair or explant.

Consequently, there is no apparatus or relatively simple, non-surgical procedure known to be available by which a physician may reliably and safely implant a genitourinary prosthesis to enable a patient to overcome urinary incontinence. While it has been suggested that urinary incontinence may be successfully treated with a periurethral injection of TEFLON paste, this treatment has been known to lead to potential problems as a result of the migration of paste particles from the injection site.

SUMMARY OF THE INVENTION

Briefly, and in general terms, a compact, hand-held instrument is disclosed to enable a physician to reliably and controllably implant, dispense and inflate an inflatable membrane at a predetermined target area within the tissue of the patient. The disclosed instrument may be used as part of a relatively simple, non-surgical procedure by which to accurately and safely implant an inflatable genitourinary prosthesis in the periurethral tissues of the corpus spongiousum, so that a patient may overcome urinary continence.

The instrument includes an associated vernier hypodermic syringe, or the like, for supplying fluid to inflate the membrane. The instrument also includes an assembly of telescoping trocar elements which may be placed in a retracted condition for dilating a tunnel through the urethral tissue of the patient or in an expanded condition for placing, dispensing and inflating the membrane. The trocar assembly comprises a pair of articulating tunneling members which enclose and protect the membrane. The tunneling members may be closed around the membrane in the expanded trocar condition to form a sharp cutting nose to penetrate the urethral tissue of the patient, or, the tunneling members may be angularly separated so that the membrane is exposed to the urethral tissue for implantation and inflation therewithin. The membrane is affixed to a hollow, non-coring needle, which needle is attached to one end of a fluid infusion tube. The other end of the fluid infusion tube communicates with the vernier hyopdermic syringe, so that a measured volume of fluid can be percutaneously infused from the syringe to the membrane by way of the fluid infusion tube and the needle. The needle and infusion tube are retracted through a coaxially arranged trocar tube, whereby the trocar tube forms a shoulder for reliably detaching an inflated membrane from the needle.

The trocar assembly is withdrawn from the patient with the inflated membrane remaining at the targeted tissue site. An inflated membrane proportionately increases local tissue volume in the ara of the periurethral tissues of the corpus spongiousum to correspondingly increase the occlusive pressure applied to the urethral tissues for restoring a patient to continence. One or more of the membranes may be implanted and inflated, depending upon etiology, degree of residual spincteric function, vascularity and physical properties of the patient's urethral tissues.

DESCRIPTION OF THE PREFERRED EMBODIMENT

Figures 1, 2A, 2B:
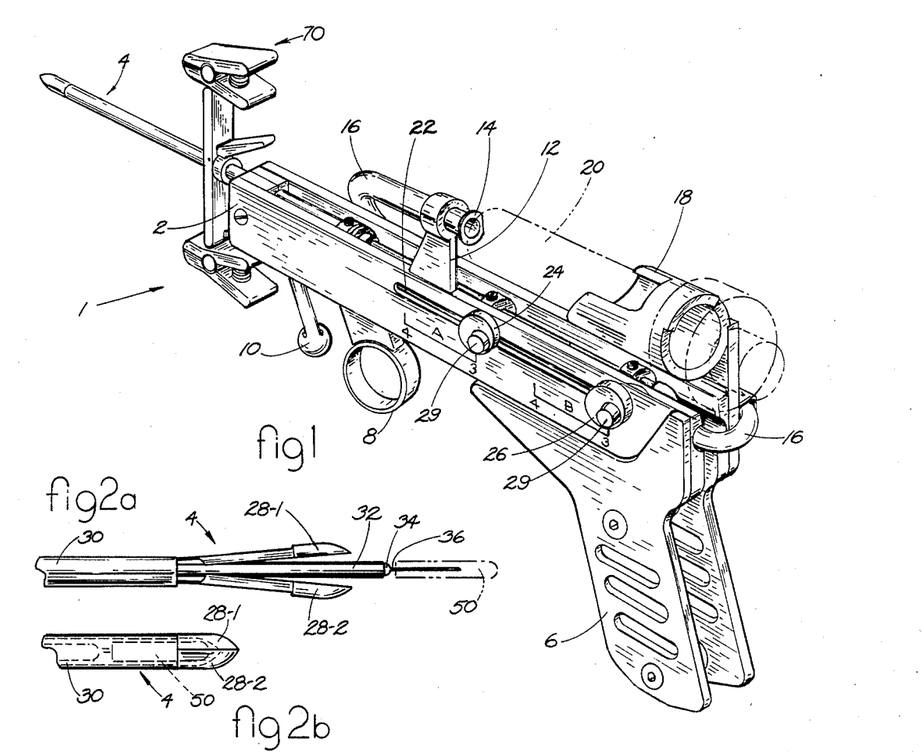
FIG. 1 shows an isometric view of the hand-held instrument which forms the present invention.
FIG. 2a shows a telescoping trocar assembly of the instrument of FIG. 1 in an expanded trocar condition.
FIG. 2b shows the trocar assembly of the instrument of FIG. 1 in a retracted trocar condition.

The hand-held instrument of the present invention for implanting, dispensing and inflating inflatable membranes is now described while referring to the drawings. Referring initially to FIG. 1, there is shown the hand-held instrument 1 which includes a control housing 2 for supporting an assembly 4 of telescoping trocar elements at one end thereof and a suitable grip or handle 6 at the opposite end. A hemostat 70 is attached to and slideable along the trocar assembly 4 for attachment to the patient's skin or to a surgical drape to increase axial instrument stability. Extending downwardly from control housing 2 is a trigger 8. Also extending downwardly from the control housing 2 ahead of trigger 8, is a trigger return lever 10. The function and operation of trigger 8 and trigger return lever 10 will be disclosed in greater detail when referring to FIG. 3. A support bracket 12 extends upwardly from one end of control housing 2. An infuser terminal 14 is connected to an inlet of a fluid transfer tube 16. Extending upwardly from the opposite end of control housing 2 is a hypodermic syringe receptacle 18. Infuser terminal 14 and syringe receptacle 18 are aligned with one another to receive and support a vernier hypodermic syringe (shown in phantom and designated 20), such that fluid may be percutaneously infused from syringe 20 by way of transfer tube 16 to inflate the inflatable membrane according to a procedure that will be described in greater detail when referring hereinafter to FIGS. 4–13. By way of example only, a vernier hypodermic syringe which has particular application for use with instrument 1 for supplying fluid to inflate a membrane is described in U.S. Pat. No. 4,710,179 issued Dec. 1, 1987, and entitle SNAP-ON VERNIER SYRINGE by Terry M. Haber, et al.

A longitudinal extending tracking slot 22 is formed in control housing 2. A retractor knob 24 and an actuator knob 26 are received within and slideable along tracking slot 22. Each of the retractor knob 24 and actuator knob 26 has a respective release button 29 which must be depressed to permit the retractor and actuator knobs 24 and 26 to slide along the slot 22. Suitable positioning indicia is marked on control housing 2 along the length of tracking slot 22 to denote certain locations to which the retractor knob 24 and actuator knob 26 are to be moved to accurately and controllably implant, dispense, and inflate a membrane within the bodily tissues of a patient.

Referring now to FIGS. 2a and 2b of the drawings, the assembly 4 of telescoping trocar elements is described. In a retracted trocar condition of FIG. 2b, a pair of normally opened, articulating clam shell-shaped tunneling members 28-1 and 28-2 are withdrawn into the trocar assembly 4 and retained in a closed configuration around an inflatable membrane 50 to protect the membrane and provide a sharp, blunt dilating nose by which to dilate a tunnel through the patient's tissue for implanting the membrane 50. In an expanded trocar condition of FIG. 2a, the clam shell-shaped tunneling members 28-1 and 28-2 are released from the trocar assembly 4 so as to be automatically opened for the purpose of permitting the membrane 50 to be positioned, dispensed, and inflated at a targeted area within the patient's tissues.

The trocar assembly 4 comprises an outer trocar sleeve 30 which functions as a nest for receiving therewithin and closing the tunneling members 28-1 and 28-2 when the assembly is retained in the retracted trocar condition of FIG. 2b. An inner trocar tube 32 is coaxially arranged with outer trocar sleeve 30. Concentrically arranged with and slideable through inner trocar tube 30 is a fluid infusion tube 34. Fluid infusion tube 34 supports a non-coring, hollow needle 36 at one end thereof and provides a fluid channel which is connected at the opposite end with the fluid transfer tube 16 (of FIG. 1) for delivering fluid to the membrane 50 via needle 36. The membrane 50 is attached to needle 36 to receive fluid supplied by the hypodermic syringe and delivered via the needle and the fluid infusion tube 34.

As is best shown in FIG. 2a, fluid infusion tube 34 has a hyperbolically-radiused base section to efficiently distribute stresses and increase resistance to breakage at the point at which non-coring needle 36 is attached. In this manner, the needle 36 will be less likely to break as a consequence of mechanical forces encountered during the placing and dispensing of membrane 50. Moreover, the coaxial arrangement of fluid infusion tube 34 and inner trocar tube 32 creates a shoulder against which membrane 50 is reliably and safely removed from the needle 36 when fluid infusion tube 34 is retracted through inner trocar tube 32 after the membrane 50 has been suitably implanted and inflated within the tissues of the patient.

Figure 3:
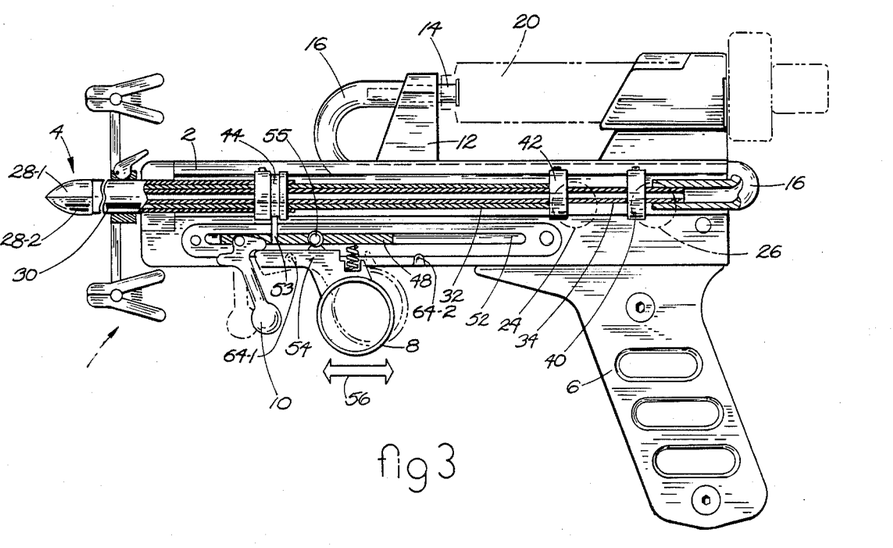
FIG. 3 shows a partial cross-section of the instrument of FIG. 1 so as to illustrate details of the trocar assembly interconnected with an associated fluidic system.

FIG. 3 of the drawings illustrates the interconnection between the fluid supply system and the assembly 4 of telescoping trocar elements of the hand-held instrument 1, so that fluid may be supplied from hypodermic syring 20 to membrane 50 (of FIG. 2a) by way of fluid transfer tube 16 and fluid infusion tube 34. More particularly, a proximal end of fluid transfer tube 16 is connected to syringe 20 at infuser terminal 14. A distal end of fluid transfer 16 is affixed to a proximal end of fluid infusion tube 34. Also connected to the proximal end of fluid infusion tube 34 is a moveable infusion tube collar 40. Infusion tube collar 40 is connected to and positioned by actuator knob 26, such that a movement of actuator knob 26 through the tracking slot 22 (of FIG. 1) causes a corresponding axial movement of both infusion tube collar 40 and infusion tube 34. Inasmuch as fluid infusion tube 34 is connected to the distal end of fluid transfer tube 16, the axial movement of fluid infusion tube 34 will also move the distal end of transfer tube 16 so as to assure an uninterrupted flow of fluid from the syringe 20 to tube 34. Fluid infusion tube 34 extends from the connection with fluid transfer tube 16, through the interior of control housing 2, to the non-coring needle 36 (of FIG. 2a). Therefore, the physician may controllably move the fluid infusion tube 34 and the needle 36 between the retracted trocar condition of FIG. 2b and the expanded trocar condition of FIG. 2a whenever the actuator knob 26 is moved back and forth along the tracking slot 22.

Surrounding fluid infusion tube 34 is the inner trocar tube 52. Connected to a first end of inner trocar tube 32 is a moveable inner trocar collar 42. Inner trocar tube collar 42 is connected to and positioned by retractor knob 24, such that a movement, by the physician, of retractor knob 24 through the tracking slot 22 (of FIG. 1) causes a corresponding axial movement of inner trocar tube 32 between the retracted trocar position of FIG. 2b and the expanded trocar position of FIG. 2a. Hence, it should be appreciated that a movement of actuator knob 26 causes fluid infusion tube 34 to slide through inner trocar tube 32 for moving the non-coring needle 35 from the expanded to the retracted trocar condition after implantation and inflation of the membrane. Moreover, the movement of retractor knob 24 causes the inner trocar tube 32 to be withdrawn from the expanded trocar condition and moved into the retracted trocar condition. Therefore, the physician may safely detach an inflated membrane from needle 36 by moving actuator knob 26 and thereby causing fluid infusion tube 34 and the needle 36 which is attached thereto to slide through inner trocar tube 32 towards the retracted trocar condition (of FIG. 2b). As previously indicated, the second end of inner trocar tube 32 forms a shoulder for engaging and detaching the membrane from the needle 36 as the fluid infusion tube 34 is retracted through the trocar tube 32.

Surrounding inner trocar tube 32 is the outer trocar sleeve 30. Connected to one end of outer trocar sleeve 30 is a moveable outer trocar collar 44. Outer trocar collar 44 has a hollow configuration for receiving and supporting the coaxial arrangement of inner trocar tube 32 and fluid infusion tube 34. Outer trocar collar 44 is connected to and positioned by a tracking plate 48. Tracking plate 48 is received within and slideable along a hollow track 52 which extends axially through control housing 2. Tracking plate 48 is connected by a rod 43 and a bearing 55 to an integral arm 54 of trigger 8. Accordingly, the operation of trigger 8 in either of the directions of reference arrow 56 causes the tracking plate 48 to slide along track 52 and outer trocar collar 44 to move outer trocar sleeve 30 into either the retracted trocar condition of FIG. 2b (for receiving and closing tunneling members 28-1 and 28-2 to form a tissue penetrating nose) or the expanded trocar condition of FIG. 2a (for releasing and thereby opening tunneling members 28-1 and 28-2 for permitting the inflation of a membrane).

Opposing detents (not shown) are formed at the rearward end of tunneling members 28-1 and 28-2 and the forward end of outer trocar sleeve 30. Hence, pulling the trigger 8 in a rearward direction causes outer trocar sleeve 30 to be moved rearwardly towards the expanded trocar condition (of FIG. 2a) so that tunneling members 28-1 and 28-2 can be released and opened. When outer trocar sleeve 30 is moved in a direction approaching the expanded trocar condition, the detents of sleeve 30 and tunneling members 28-1 and 28-2 will eventually engage one another to withdraw the opened tunneling members away from, and thereby expose, the non-coring needle 36 for attachment to or inflation of the membrane. Likewise, pushing the trigger 8 in a forward direction causes outer trocar condition (of FIG. 2b) to thereby return outer trocar sleeve 30 to a position at which to retain and close the tunneling members 28-1 and 28-2.

Trigger return lever 10 is pivotally connected to tracking plate 48, such that lever 10 will ride along with trigger 8 whenever the trigger is moved in either of the directions indicated by reference arrow 56. Trigger 8 travels between forward and rearward indexing notches 64-1 and 64-2 formed in the bottom of control housing 2 to mve the outer trocar sleeve 30 between the retracted and expanded trocar conditions. However, trigger 8 must first be rotated out of an indexing notch 64-1 and 64-2 (against the bias of an associated spring) before the trigger can be pulled rearwardly or returned forwardly along control housing 2. Trigger retrun lever 10 may be locked to form a stop when the trigger 8 is located at the rearward indexing notch 64-2 to prevent an inadvertent return of the trigger to the forward indexing notch 64-1 and a premature closing of tunneling members 28-1 and 28-2. That is, trigger return lever 10 must be rotated to an unlocked position (shown in phantom) in order to permit the physician to rotate trigger 8 out of the rearward indexing notch 64-1 for moving trigger 8 forwardly for the purpose of closing tunneling members 28-1 and 28-2.

Figure 4:
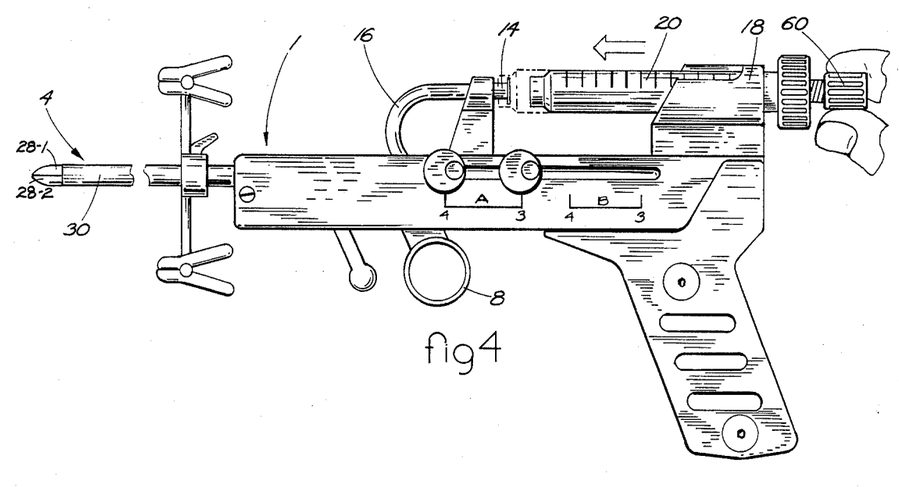
FIGS. 4-13 illustrate the steps for operating the present instrument for implanting, dispensing and inflating an inflatable membrane.
Figure 5:
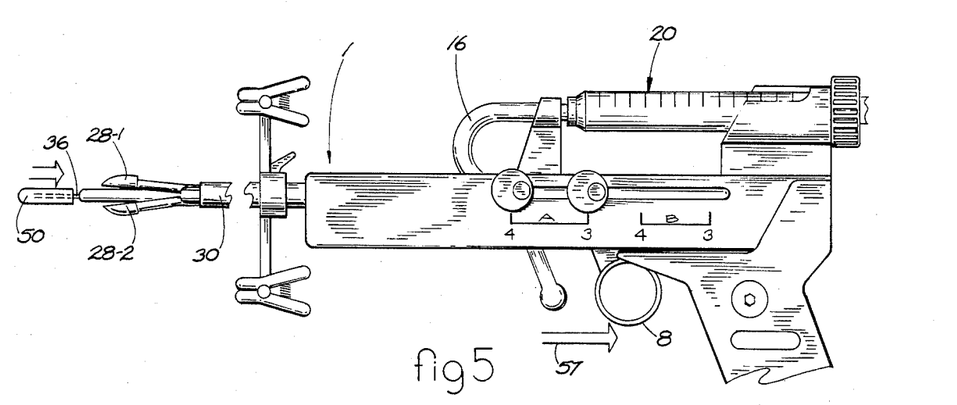

The operation of the hand-held instrument 1 for implanting, dispensing and inflating the inflatable membrane 50 is described while referring to FIGS. 4-13 of the drawings. Referring first to FIGS. 4 and 5, the retractor knob 24 and actuator knob 26 of instrument 1 are initially moved to forward positions along tracking slot 22 (designated by indicia marked A4 and A3, respectively). The telescoping members of trocar assembly 4 are initially in a retracted trocar condition, and tunneling members 28-1 and 28-2 are closed to form the blunt dilating cutting nose. The physician, using sterile procedures, then fills vernier hypodermic syringe 20 with a suitable biocompatible fluid (e.g. a radio opaque isotonic fluid, isotonic saline solution, or the like). However, it is to be expressly understood that use of a fluid in this invention is not to be regarded as a limitation, and the syringe 20 may alternatively be filled with a suspension of particulate matter, particles, and the like. Once the hypodermic syringe 20 is filled, it is placed in the instrument 1, as previously indicated, between infuser terminal 14 and syringe receptacle 18.

To attach a membrane to the telescoping trocar assembly 4, the trigger 8 is pulled rearwardly (in the direction of reference arrow 57 of FIG. 5) to simultaneously retract outer trocar sleeve 30 and tunneling members 28-1 and 28-2 so as to expose the non-coring needle 36 of fluid infusion tube 34. Holding the instrument 1 in an upright, vertical position, the physician rotates a control knob 60 (best shown in FIG. 4) of syringe 20 whereby fluid is infused from the syringe to needle 36 by way of fluid transfer tube 16 and fluid infusion tube 34 to purge any trapped air from the fluidic system of the instrument 1. Using sterile procedures, the physician affixes an uninflated membrane 50 to the needle 36 by piercing a core of membrane 50 with needle 36 and pressing the membrane onto the needle until forwrad movement of the needle is blocked by a concave surface of a self-contained metallic needle stop (not shown).

In accordance with a preferred embodiment of this invention, the membrane 50 is an elastic, elliptoidally-shaped genitourinary prosthesis, such as that disclosed in U.S. patent application Ser. No. 881,829 filed July 3, 1986. The prosthesis is formed from a tear-resistant, biocompatible material, such as, for example, polyurethane, silicone, latex, or the like. Accordingly, the teachings of said patent application regarding the genitourinary prosthesis membrane 50 and the receipt of needle 36 through a core and by a needle stop of membrane 50 are incorporated herein by reference.

Figure 6:
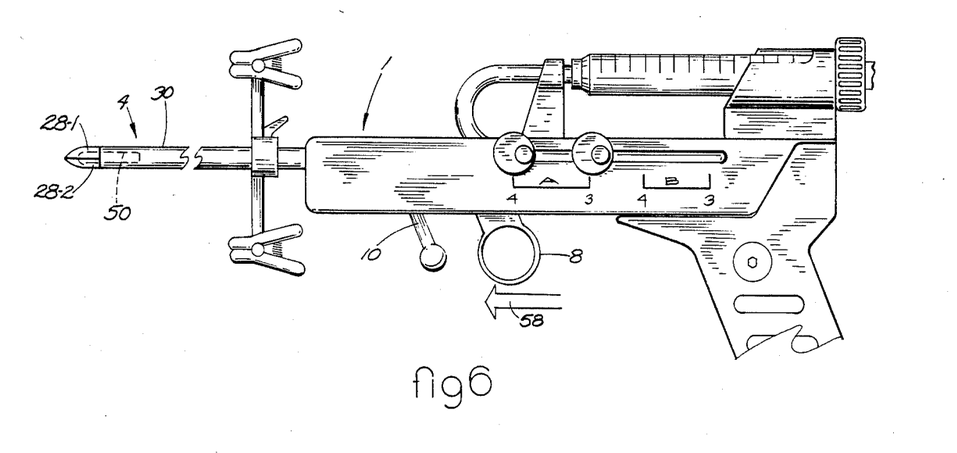

Referring now to FIG. 6, the physician rotates the trigger return lever 10 (in the direction of reference arrow 58) to permit trigger 8 to move forwardly for placing the trocar assembly 4 back in the retracted trocar condition, whereby tunneling members 28-1 and 28-2 are retained within outer trocar sleeve 30 and closed around the installed membrane 50. The instrument 1 is now ready to enable the physician to implant the membrane 50 within the bodily tissues of the patient.

Figure 7:
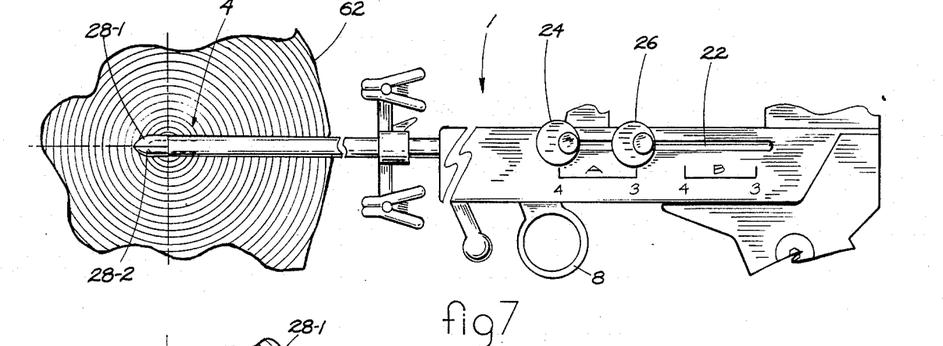
Figure 8:
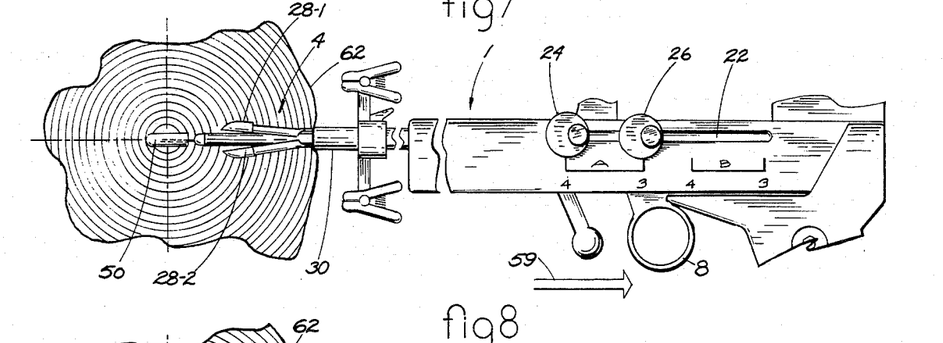

In FIG. 7, the dilating nose of instrument 1 (as formed by tunneling members 28-1 and 28-2 of trocar assembly 4) is inserted into the patient's tissue. Radiographic, fluoroscopic, cystoscopic, tactile or other conventional means may be used to navigate the dilating nose into position at the patient's implant target site. In accordance with another preferred embodiment of this invention, the target site is located in the periurethral tissues of the proximal corpus spongiousum of the patient at which the physician may implant and inflate the membrane 50 to thereby enable the patient to overcome urinary incontinence by means of increasing both localized tissue volume at and passive occlusive pressure of the periurethral tissues. Therefore, the physician exerts a force upon the instrument 1 sufficient to transurethrally or perineally insert the dilating nose of trocar assembly 4 to bluntly disect a small tunnel through the patient's urethral tissue 62.

In FIG. 8, the physician once again pulls the trigger 8 in a rearward direction (in the direction of reference arrow 59) for placing the trocar assembly 4 of instrument 1 in the expanded trocar condition of FIG. 2a. In the expanded trocar condition, the outer trocar sleeve 30 is withdrawn and the tunneling members 28-1 and 28-2 are released and pulled away from membrane 50 by the sleeve 30. Accordingly, the tunneling members are opened so as to expose the previously attached and uninflated membrane 50 to the patient's urethral tissue 62.

Figure 9:
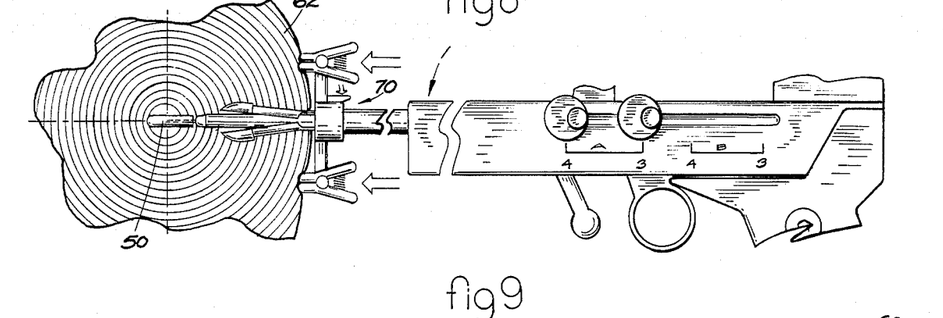
Figure 10:
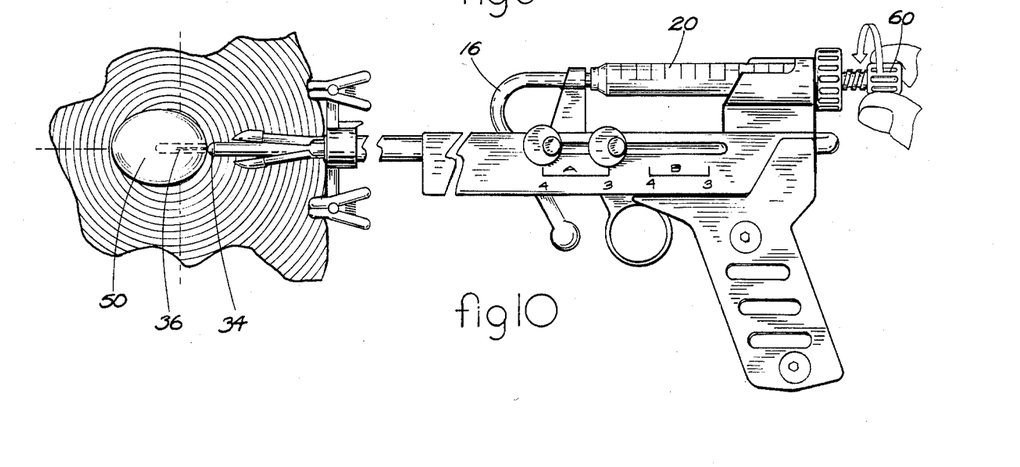

In FIG. 9, the physician clamps the sliding hemostat 70 to the patient's skin and/or to a surgical drape (not shown) to stabilize the instrument 1 against axial movements, either proximally or distally, and permit the physician to inflate the membrane 50 at the precise designated target area within the patient's urethral tissue 62. Next, and referring to FIG. 10, the physician inflates the membrane 50 by percutaneously infusing an incrementally regulated amount of fluid (or solid matter) from the vernier hypodermic syringe 20 to the interior of the membrane 20. The foregoing is accomplished when the physician rotates the control knob 60 of syringe 20 (or otherwise operates a conventional syringe) to force an appropriate volume of fluid from the syringe and through the fluid system of instrument 1 comprising fluid transfer tube 16, fluid infusion tube 34, and non-coring needle 36. The physician may then radiographically and/or cystoscopically ensure that the membrane 50 is accurately positioned and properly inflated to generate sufficient occlusive pressure for enabling the patient to overcome incontinence.

Figure 11:
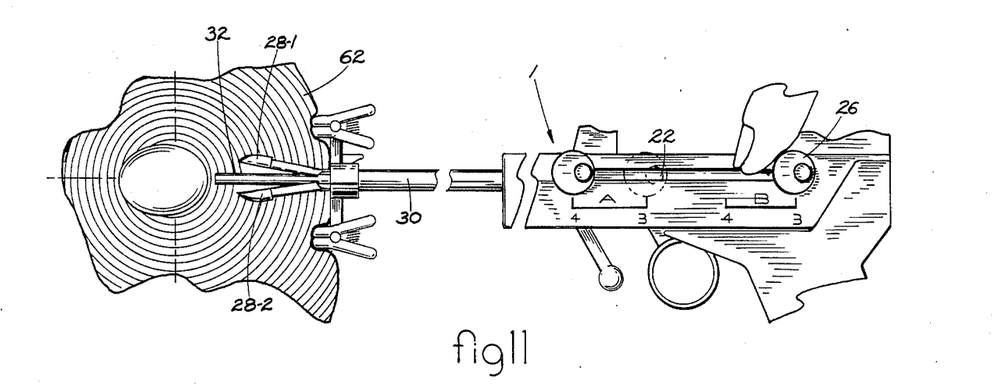

In FIG. 11, the physician detaches a deflated membrane 50 from the needle (36 in FIG. 10) and withdraws such needle and the fluid infusion tube (34 in FIG. 10) through the inner trocar tube 32. To accomplish the foregoing, the physician slides actuator knob 26 out of its initial forward position (designated by indicia marked A3) to a final rearward position along tracking slot 22 (designated by indicia marked B3). As best disclosed when earlier referring to FIG. 3, the rearward movement of actuator knob 26 along slot 22 withdraws the fluid infusion tube 34 through inner trocar tube 32 and safely detaches the inflated membrane 50 from needle 36 against the shoulder formed by coaxially arranged trocar tube 32. However, the inflated membrane remains precisely at its position of placement within the targeted (i.e. urethral) tissues 62 of the patient.

Figure 12:
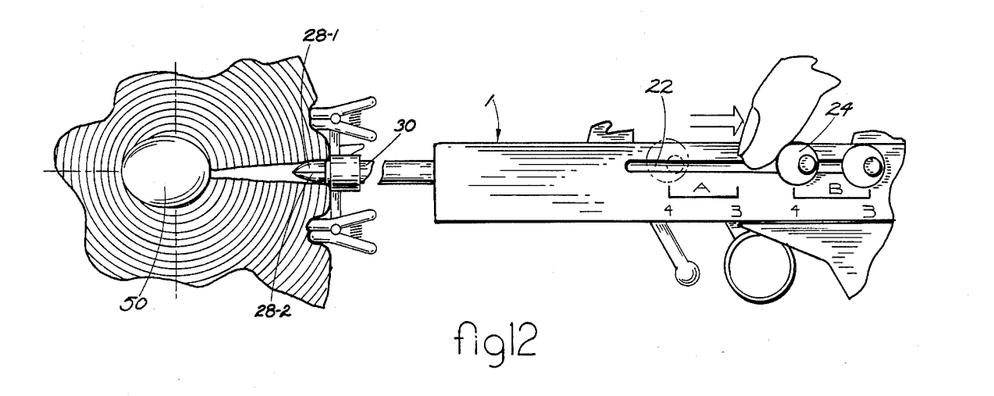
Figure 13:
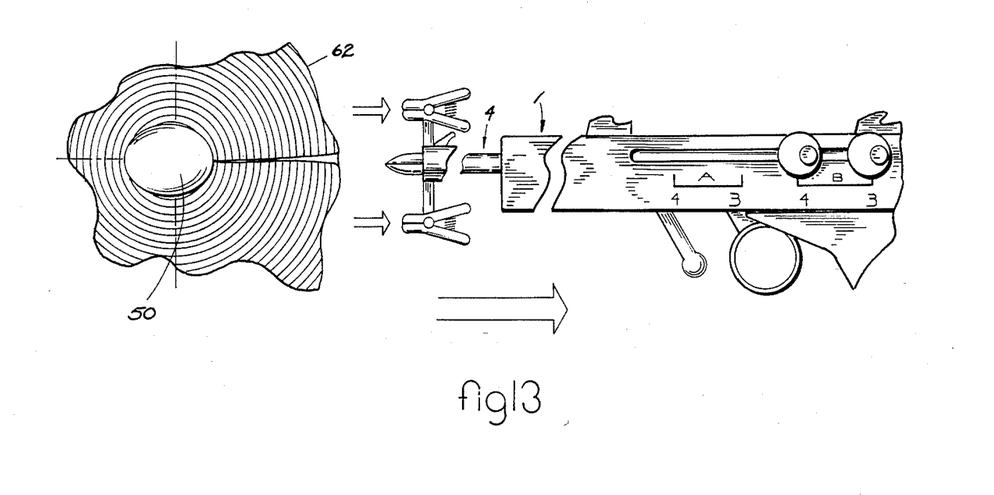

In FIG. 12, the physician withdraws the inner trocar tube 32 by sliding retracter knob 24 out of its initial forward position (designated by indicia marked A4) to a final rearward position along tracking slot 22 (designated by indicia marked B4). Inner trocar tube 32 also has detents (not shown) which engage the tunneling members 28-1 and 28-2 to simultaneously retract such members into outer trocar sleeve 30. The trocar assembly 4 of instrument 1 is then withdrawn from the urethral tissues 62 in FIG. 13 without disturbing the condition or position of the inflated membrane 50. Inasmuch as only a small wound remains after withdrawal of trocar assembly 4, a single skin suture placed at the center of the wound should be sufficient to close the patient's tissue.

Figure 14:
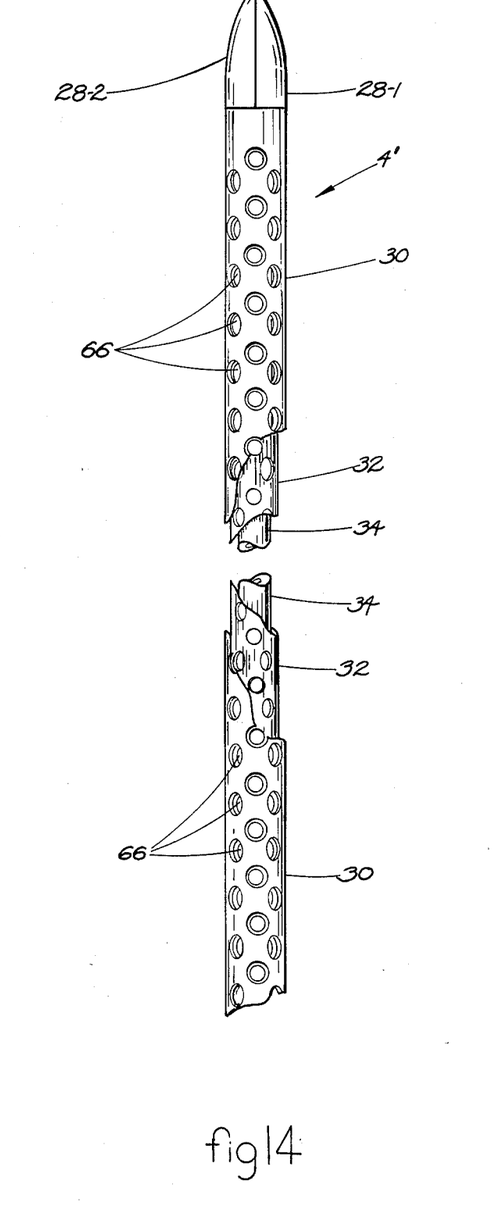
FIG. 14 shows an alternate trocar assembly including a matrix of perforations through which to pass a sterilizing liquid or gas.

FIG. 14 of the drawings shows an alternate trocar assembly 4' to be used in the instrument 1 of FIG. 1. More particularly, both the outer trocar sleeve 30 and the inner trocar tube 32 are provided with a matrix of perforations or apertures 66 through which a sterilizing liquid or gas may pass for reliably and conveniently sterilizing the telescoping members of the trocar assembly 4'. For example, sterilizing gases such as ethylene oxide or sterilizing solutions such as Cidex or betadine may be passed through the perforations 66. Sterilization of trocar assembly 4' may also be accomplished in a conventional autoclave, where the perforations 66 will permit an efficient circulation of sterilizing steam between trocar sleeve 30, trocar tube 32 and infusion tube 34.

Although the presently disclosed instrument has been explained with reference to implanting, dispensing and inflating a single membrane 50, it is to be expressly understood that any number of such membranes may be implanted, depending upon the increased tissue volume and resulting occlusive pressure which are required to permit a patient to be restored to cntinence. During and after one or more genitourinary prostheses have been implanted, the physician may cystoscopically monitor the patient's degree of coaptation of the urethral mucosa. In the event that greater occlusive pressure is needed, the physician may implant a corresponding additional number of prostheses until patient continence is restored.

It will be apparent that while a preferred embodiment of the invention has been shown and described, various modifications and changes may be made without departing from the true spirit and scope of the invention. For example, the instrument 1 has applications other than for implanting an inflatable membrane for use as a genitourinary prosthesis to enable a patient to overcome incontinence. More particularly, the hand-held instrument disclosed herein may also be used to implant a selectively permeable (by a gas or liquid) membrane which may function as a drug delivery system. Other applicatins include an instrument for implanting a variable volume mass to replace surgically removed tissue and/or organ excisions or an injectable anti-ureteral reflux mass. Still further applications of the present invention include an instrument for implanting a testicular prosthesis, an injectable closure blockage for arteries and veins, a prosthetic sphincter, and an injectable intraocular lens. Of course, the inflatable membrane described in this invention is also applicable for controllably occluding luminal passages other than the patient's urethra when it is necessary to selectively control the flow of material therethrough.

Having thus set forth a preferred embodiment, what is claimed is:

1. An instrument for implanting an inflatable genitourinary prosthesis within the urethral tissues of a patient to increase local tissue density and the application of occlusive pressure at the periurethral tissues of the corpus spongiousum for treating urinary incontinence, said instrument including an inflatable genitourinary prosthesis, means for inflating said prosthesis with material, and trocar assembly means comprising:
   an infusion tube extending between said inflating means and said prosthesis to deliver material for inflating said prosthesis;
   a pair of normally open tunneling members for dilating a tunnel through the urethral tissues, said tunneling members movable to either a closed position to surround and protect an uninflated prosthesis and thereby form a tissue dilating nose or to an open position to permit said prosthesis to be inflated and positioned within the urethral tissues; and
   an outer trocar sleeve movable to a first position to surround and engage said tunneling members to retain said members in the closed position to form said dilating nose or to a second position retracted from said tunneling members to release said members for movement to the open position to permit inflation of said prosthesis.

2. The instrument recited in claim 1, said trocar assembly further comprising an inner trocar tube concentrically arranged with respect to each of said infusion tube and said outer trocar sleeve, such that said infusion tube is slideable through said inner trocar tube and said inner trocar tube is slideable through said outer trocar sleeve;
   said prosthesis removably supported at one end of and being detachable from said infusion tube after inflation of said prosthesis so as to be positioned within the urethral tissues of the patient when said infusion tube is slideably withdrawn through said inner trocar tube.

3. The instrument recited in claim 2, wherein said inner trocar tube and said outer trocar sleeve are provided with a plurality of perforations through which a sterilizing fluid or gas may pass for sterilizing said inner trocar tube, said outer trocar sleeve, and said infusion tube.

4. An instrument for implanting, dispensing and inflating an inflatable membrane within subcutaneous tissue of a patient, said instrument comprising:
   carrying means to which said membrane is removably attached;
   a source of material communicating with said membrane to inflate said membrane after said membrane is implanted within the patient's tissue;
   dilating means for cutting a tunnel through the patient's tissue, said dilating means disposed in either a closed condition to surround and protect an uninflated membrane whereby to form a dilating nose for penetrating the patient's tissue or an open condition whereby to permit said membrane to be dispensed and inflated; and
   an outer sleeve surrounding said dilating means and slidable axially thereon, said outer sleeve moveable to either an axially extended position at which to close said dilating means around said membrane to form said dilating nose or to an axially retracted position at which to release said dilating means to the open condition for dispensing said membrane.

5. The instrument recited in claim 4, wherein said dilating means includes a pair of articulating members adapted to be disposed in either of said closed or open conditions depending upon the position of said outer sleeve relative thereto.

6. The instrument recited in claim 4, wherein said means for carrying said membrane includes a hollow needle, said membrane communicating with said source of material by way of said needle so that an uninflated membrane may be inflated when said dilating means is disposed in the open condition.

7. The instrument recited in claim 6, further comprising an inner tube coaxially aligned with and slidable axially through said outer sleeve; and
   an infusion tube coaxially aligned with and slidable axially through said inner tube, said infusion tube extending between said source of material and said hollow needle for supplying material to said membrane, said needle being attached to and supported from one end of said infusion tube.

8. The instrument recited in claim 7, wherein said inner tube and said outer sleeve are provided with a plurality of perforations through which a sterilizing fluid or gas may pass for sterilizing said inner tube, said outer sleeve, and said infusion tube.

9. The instrument recited in claim 7, further comprising means for moving said infusion tube axially through said inner tube from an axially extended position at which to inflate said membrane to an axially retracted position by which to detach said inflated membrane from said needle when said infusion tube is moved through said inner tube.

10. The instrument recited in claim 9, further comprising first, second, and third positin control means respectively coupled to said outer sleeve, said inner tube, and said infusion tube, said position control means being slidable axially along said instrument to correspondingly control the movements of said outer sleeve, inner tube, and infusion tube relative to one another.

11. The instrument recited in claim 10, further comprising a plurality of guide slots extending axially along said instrument, said position control means being received in and slidable through respective ones of said guide slots to control the movements of said outer sleeve, said inner tube, and said infusion tube relative to one another.

12. The instrument recited in claims 4, wherein said inflatable membrane is an elastic genitourinary prosthesis and the subcutaneous tissue is the periurethral tissues of the corpus spongiousum, said prosthesis being implanted and inflated for the treatment of urinary incontinence.

13. The instrument recited in claims 4, wherein said source of material for inflating said membrane is a hypodermic syringe.

14. A hand-held instrument comprising a plurality of telescoping tubular members by which to implant, dispense and inflate an inflatable membrane within the subcutaneous tissues of a patient, said instrument comprising:
   an elastic, inflatable membrane;
   a source of material communicating with said membrane to inflate said membrane after said membrane has been implanted within the patient's tissue,
   dilating means for cutting a tunnel through the patient's tissue, said dilating means disposed in either a closed condition to surround and protect an uninflated membrane, whereby to form a dilating nose for penetrating the patient's tissue or an open condition, whereby to permit said membrane to be dispensed and inflated;

an outer sleeve surrounding said dilating means and slidable axially thereover, said outer sleeve movable to either an axially extended position at which to close said dilating means around said membrane to form said dilating nose or to an axially retracted position at which to release said dilating means to the open condition for dispensing said membrane;

an inner tube coaxially aligned with and slidable axially through said outer sleeve; and an infusion tube coaxially aligned with and slidable axially through said inner tube and extending between said source of material and said membrane for supplying material from said source to inflate said membrane.

15. The instrument recited in claim 14, further comprising a hollow hypodermic needle attached to and supported from one end of said infusion tube, said membrane being detachably connected to said needle, such that material for inflating said membrane is supplied from said source thereof to said membrane by way of said infusion tube and said needle.

16. The instrument recited in claim 14, wherein said dilating means includes a pair of articulating members adapted to be disposed in either of the closed or open conditions depending upon the position of said outer sleeve relative thereto.

17. The instrument recited in claim 14, wherein said membrane is detachably connected to one end of said infusion tube.

18. The instrument recited in claim 17, further comprising:
  means to retract said outer sleeve from said dilating means to release said dilating means to the open condition;
  means to withdraw said infusion tube through said inner tube after said membrane is inflated, said inner tube forming a shoulder against which said membrane is moved for detaching said membrane from said infusion tube; and
  means to withdraw said inner tube through said outer sleeve after said infusion tube is withdrawn through said inner tube.

19. The instrument recited in claim 18, wherein said means to retract said outer sleeve, said means to withdraw said infusion tube, and said means to withdraw said inner tube are respectively coupled to said outer sleeve, said infusion tube, and said inner tube and are adapted for axial movement along said instrument to control the movement of said outer sleeve, said infusion tube, and said inner tube relative to one another.

20. The instrument recited in claim 19, further comprising a plurality of guide slots extending axially along said instrument, said means to retract said outer sleeve, said means to withdraw said infusion tube, and said means to withdraw said inner tube being received in and slidable through respective ones of said slots to control the movements of said outer sleeve, said infusion tube, and said inner tube relative to one another.

* * * * *